United States Patent
Abumrad et al.

(10) Patent No.: US 6,316,693 B1
(45) Date of Patent: Nov. 13, 2001

(54) TRANSGENIC MOUSE MODEL FOR FATTY ACID TRANSPORT

(75) Inventors: Nada Abumrad, Cold Spring Harbor; Azeddine Ibrahimi, Setauket; Christopher M. Picken, Sayville, all of NY (US)

(73) Assignee: The Research Foundation of the State University of New York, Stony Brook, NY (US)

( * ) Notice: Subject to any disclaimer, the term of this patent is extended or adjusted under 35 U.S.C. 154(b) by 0 days.

(21) Appl. No.: 09/162,098

(22) Filed: Sep. 28, 1998

Related U.S. Application Data (60) Provisional application No. 60/061,734, filed on Oct. 2, 1997.

(51) Int. Cl.[7] .................... G01N 33/00; C12N 15/09; C12N 5/00
(52) U.S. Cl. .................... 800/18; 800/3; 800/14
(58) Field of Search .................... 800/8, 9, 13, 18, 800/3, 25, 14; 435/325, 320.1, 69.1, 455; 536/23.1, 23.51, 24.1

(56) References Cited

PUBLICATIONS

"Heart CD36 Expression Is Increased In Murine Models Of Diabetes And In Mice Fed A High Fat Diet" (Dale E. Greenwalt et al., ); J. Clinical Investigation, Inc., vol. 96, 1382–1388, Sep. 1995).

"Expression Of The CD36 Homolog (FAT) In Fibroblast Cells: Effects On Fatty Acid Transport" (Azeddine Ibrahimi et al.); Proc. Natl. Acad. Sci USA, vol. 93, pp. 2646–2651, Apr. 1996.

"Cloning Of A Rat Adipocyte Membrane Protein Implicated In Binding Or Transport Of Long–chain Fatty Acids That Is Induced During Preadipocyte Differentiation" (Nada A. Abumrad et al.); The Journal of Biological Chemistry, vol. 268, No. 24, pp. 17665–17668, Aug. 25, 1993.

"Putative Membrane Fatty Acid Translocase And Cytoplasmic Fatty Acid–Binding Protein are Co–Expressed In Rat Heart And Skeletal Muscles" (F.A. Van Nieuwenhoven et al.); Biochemical And Biophysical Research Communications, vol. 207, No. 2, Feb. 15, 1995.

"Native And Modified Low Density Lipoproteins Increase The Functional Expression Of The Macrophage Class B Scavenger Receptor, CD36" (Jihong Han et al.); The Journal Of Biological Chemistry, vol. 272, pp. 21654–21659, Aug. 22, 1997.

"Prevention Of Diet–Induced Obesity In Transgenic Mice Overexpressing Skeletal Muscle Lipoprotein Lipase" (D.R. Jensen et al.); The American Physiological Society, R683–R689, 1997.

"Expression Of A Dominant–Negative Mutant Human Insulin Receptor In The Muscle Of Transgenic Mice" (Pi–Yun Chang et al.); The Journal of Biological Chemisty, vol. 269, No. 23, pp. 16034–16040, Jun. 10, 1994.

"Regulation Of FAT/CD36 Gene Expression: Further Evidence In Support Of A Role Of The Protein In Fatty Acid Binding/Transport" (Z. Sfeir et al.); Prostaglandins, Leukotrienes and Essential Fatty Acids, 57(1), 17–21, Pearson Professional Ltd., 1997.

"Regulation Of Fatty Acid Transport Protein And Fatty Acid Translocase mRNA Levels By Endotoxin And Cytokines" (Riaz A. Memon et al.); The American Physiol. 274: E210–E217, 1998.

"Is CD36 Deficiency An Etiology Of Hereditary Hypertrophic Cardiomyopathy" (Takao Tanaka et al.); J. Mol. & Cellular Cardiology 29: 121–127 (1987).

Expression Of Putative Fatty Acid Transporter Genes Are Regulated By Peroxisome Proliferator–Activated Receptor α and κ Activators In a Tissue– And Inducer–Specific Manner* (Kiyota Motojima et al.); The Journal Of Biological Chemistry, vol. 273, No. 27, pp. 16710–16714, Jul. 3, 1998.

Levak–Frank et al., J. Clin. Invest., 96:976–986, 1995.*

Palmiter et al., Proc. Natl. Acad. Sci. USA, 88:478–482, 1991.*

Whitelaw et al., Transgenic Research, 1:3–13, 1991.*

Colman, Am. J. Clin. Nutr., 63:639S–645S, 1996.*

Palmiter, An. Rev. Genet., 20:464–499, 1986.*

Wall, Theriogenology, 45:57–68, 1996.*

* cited by examiner

*Primary Examiner*—Deborah J. R. Clark
*Assistant Examiner*—Janet M Kerr
(74) *Attorney, Agent, or Firm*—Scully, Scott, Murphy & Presser (57) ABSTRACT

The present invention is directed toward a transgenic mouse comprised of germ cells and somatic cells which contain a recombinant CD36 gene operatively linked to a muscle creatine kinase promoter. Overexpression of the recombinant CD36 gene in muscle tissue promotes localized (tissue-specific) and systemic changes in fatty acid metabolism, overall body fat and weight gain in the animal.

(2 of 8 Drawing Sheet(s) Filed in Color)

PANEL A
(Control)

Figure 5A

PANEL B
(MCK-CD36)

Figure 5B

PANEL A
(Control)

Figure 6A

PANEL B
(MCK-CD36)

Figure 6B

TRANSGENIC MOUSE MODEL FOR FATTY ACID TRANSPORT

CROSS REFERENCE TO RELATED APPLICATION

This application claims the benefit of U.S. Provisional Application No. 60/061,734 filed Oct. 2, 1997.

FIELD OF THE INVENTION

This invention relates to transgenic animals which overexpress a fatty acid transporter molecule in tissues active in fatty acid utilization.

BACKGROUND OF THE INVENTION

Long-chain fatty acids (FA) have multiple properties and functions. FA are important substrates for phospholipids, which are essential membrane components. FA are also substrates for prostaglandins, which have a variety of regulatory effects. For most cells FA constitute a main source of energy. FA also directly regulate a variety of biological processes. For example, FA modulate ion channel activation, enzyme function and synaptic transmission. More recently FA have been shown to have regulatory effects on the expression of various genes, especially those encoding proteins active in lipid metabolism.

In view of the diverse functionality of FA, researchers believe that FA play a central role in the pathophysiology of multiple conditions, such as diabetes and obesity, for example. FA also contribute to insulin insensitivity and to the prevalence of vascular and coronary diseases. High levels of circulating blood FA are also associated with diabetes, many forms of obesity and hyperlipidemias. High levels of blood FA are believed to contribute to an increased production of low-density lipoproteins by the liver. Cholesterol from lipoproteins is esterified with free FA by macrophages in the vascular wall yielding cholesteryl ester which accumulates and leads to the formation of lipid-filled macrophages, precursors of atherosclerotic lesions.

The wide range of effects and physiological functions of FA underscore the importance of understanding how cellular FA uptake is regulated.

The mechanism of FA transfer across cell membranes has long been postulated to occur by simple diffusion. However, most recent biophysical studies indicate that FA diffusion may not be fast enough to accommodate FA uptake by cells active in FA metabolism. Furthermore, FA circulate in blood tightly bound to serum albumin which markedly limits FA partition into membrane lipid. Therefore the quantity of free FA that is available for cellular uptake is extremely low, i.e. in the nanomolar range.

Ibrahimi, et al. (1996) *Proc. Natl. Acad. Sci. USA* 93:2646–2651, provide biochemical evidence to support the involvement of a membrane carrier which mediates cellular uptake of long chain FA. Specifically, an 88-kDa membrane protein has been identified and isolated. This high-affinity long-chain FA transporter isolated from mice is highly homologous to human CD36. Recently, Abumrad, et al. (1993) *J. Biol. Chem.* 268(24):17665–17668, showed that CD36 was highly expressed in tissues active in FA utilization such as the heart, adipose tissue and intestine. CD36 is absent from the brain which does not utilize long-chain FA. CD36 is highly expressed in red oxidative muscle but not in white glycolytic muscle. CD36 is upregulated during muscle development and muscle stimulation when FA utilization increases, (see, Sfeir, et al. (1997) *Prostaglandins, Leukotrienes and Essential Fatty Acids* 57(1):17–21).

Han, et al. (1997) *J. Biol. Chem.* 272(34):21654–21659 studied the impact of lipids on the expression of CD36 and found that low density lipoproteins induced CD36 expression in a murine macrophage cell line. Han, et al. suggest the use of "knockout" mice that lack the expression of CD36 to assess the in vivo function of CD36 receptors.

Van Nieuwenhoven, et al. (1995) *Biochem. and Biophys. Res. Comm.* 207(2):747–752 report expression of CD36 in muscle tissue and cell types with high fatty acid metabolism and suggest a role of CD36 in fatty acid metabolism when co-expressed with another protein known as cytoplasmic fatty acid-binding protein (FABP).

Until now, there have been no satisfactory animal models in which tissue-specific overexpression of a protein and concomitant increased transport of FA can be made to occur in a reliable and predictable fashion in a substantial proportion of animals.

The mouse model of the present invention can be reliably and predictably used to assess whether overexpression of CD36 in muscle can reverse hyperlipidemias, decrease obesity, improve insulin sensitivity and lower the risk of atherosclerosis.

SUMMARY OF THE INVENTION

The present invention is directed toward a transgenic non-human vertebrate animal comprised of germ cells and somatic cells which contain a recombinant gene which is substantially homologous to a human adipocyte membrane glycoprotein, CD36. Overexpression of the CD36 gene in a tissue promotes localized (tissue-specific) and systemic changes in fatty acid metabolism in the animal.

In one aspect of the present invention the non-human vertebrate animal is a mammal such as a rodent, e.g. a mouse.

In another aspect of the present invention the recombinant gene is introduced into the animal at an embryonic stage.

In still another aspect of the present invention the recombinant gene is substantially homologous with a naturally occurring CD36 gene.

In yet another aspect of the present invention transcription of the recombinant gene is under control of an active promoter sequence which promotes gene expression in muscle tissue.

In one aspect the animals of the present invention can be used as models to test for agents potentially useful in the treatment of hyperlipidemia, obesity, diabetes and atherosclerosis.

In another aspect the animals of the invention can also be used as a source of cells for cell culture.

BRIEF DESCRIPTION OF THE DRAWINGS

The patent or application file contains at least one drawing executed in color. Copies of this patent or patent application with color drawing(s) will be provided by the office upon request and payment of the necessary fee.

DETAILED DESCRIPTION OF THE INVENTION

The present invention is directed to a transgenic non-human vertebrate animal comprising germ cells and somatic cells which contain a recombinant gene which is substantially homologous to a human adipocyte membrane glycoprotein, CD36. The animal is preferably a mouse since only mice are used for transgenic work.

A preferred transgenic mouse comprises germ cells containing a recombinant CD36 gene which is operably linked to a promoter effective for the expression of CD36 in the muscle tissue of the mice. Expression of the CD36 gene is also effective for reduction of plasma lipid levels in the mouse. The CD36 gene is preferably introduced into the mouse at an embryonic stage.

The recombinant gene is introduced into the animal, or ancestor of the animal at an embryonic stage. A preferred embryonic stage is the one-cell or fertilized oocyte stage. The recombinant gene is substantially homologous with the human adipocyte membrane glycoprotein, CD36. By "substantially homologous" is meant a gene whose encoded amino acid sequence has greater than about 80% homology to the naturally occurring vertebrate CD36 gene.

Transcription of the recombinant gene is under the control of a promoter sequence. A preferred promoter sequence actively directs expression of CD36 to specific tissues which may utilize fatty acid. A most preferred promoter sequence is mouse creatine kinase (MCK) which directs expression to muscle tissues. Muscle tissues depend on FA for a large part (60%–70%) of their energy needs. Other tissues that utilize FA include adipose, liver, heart and intestinal.

Introduction of the recombinant gene at the fertilized oocyte stage ensures that the gene sequence will be present in all of the germ cells and somatic cells of the transgenic "founder" animal. A transgenic "founder" animal is herein defined as the animal into which the recombinant gene is introduced at the one cell mouse embryo stage.

For the first time, the inventors have constructed a transgenic animal which overexpresses CD36 in muscle tissues, heart and skeletal muscle. Muscle tissue which overexpresses CD36 causes decreases in body weight, free fatty acid levels, overall body fat and cholesterol levels, for example. The results achieved by the present invention are analogous to the effects of physical activity, e.g. exercise on muscle tissue. CD36 overexpression has now been correlated, by the present inventor, with fatty acid uptake and utilization by muscle tissue. The present inventors have also discovered decreased plasma fatty acid levels and triglyceride levels correlate with increased clearance of blood fatty acid and triglycerides by muscle tissue thereby decreasing the amount of hepatic lipoprotein triglyceride produced. Decreased lipoprotein production is then correlated with decreased circulating cholesterol.

The animals of the present invention can be used as models to test for agents potentially useful in the treatment of hyperlipidemia, obesity, diabetes, atherosclerosis, and conditions where FA utilization by muscle is inadequate or could be increased to benefit the animal, for example. The agent to be tested can be administered to an animal of the invention and fatty acid utilization conventionally monitored.

The animals of the invention can also be used as a source of cells for cell culture. Cells from the animals may exhibit desired properties of both normal and transformed cultured cells, i.e. the cells will be normal or nearly normal morphologically and physiologically, but can, like NIH3T3 cells for example, be cultured for extended periods of time.

The invention will now be illustrated by means of the following non-limiting examples.

EXAMPLE 1

Production of CD36 Fused Genes

An expressible minigene of the invention was constructed in accordance with conventional techniques, described by Ausubel, et al. (1987) *Current Protocols in Molecular Biology* (Greene & Wiley, New York), incorporated herein by reference. A 1.7 kb fragment containing 1.3 kb of the CD36 coding sequence and the polyadenylation signal described in Abumrad, et al. (1993) *J. Biol. Chem.* 268(24) :17665–17668 (incorporated herein by reference), were cloned in the plasmid pBluescript under the control of the regulatory sequences of the mouse creatine kinase gene (MCK) as described by Frank, et al. (1995) *J. Clin. Invest.* 96:976–986, incorporated herein by reference. The complete MCK-CD36-minigene cloned in the pBluescript plasmid (designated pBS-MCK-CD36, ATCC # PTA-2727, deposited on Nov. 27, 2000 with American Type Culture Collection, 10801 University Boulevard, Manassas, Va. 20110–2209, U.S.A.) was prepared in accordance with techniques readily appreciated by the skilled artisan. A linear DNA fragment (MCK-CD36) was isolated from the plasmid by restriction, digestion and electroelution.

EXAMPLE 2

Production of Transgenic Mice Containing MCK-CD36 Fusions

The above MCK-CD36 fusions were incorporated into the germ cells of mice as follows. A linear piece of DNA encompassing the complete MCK-CD36-minigene was injected into the male pronucleus of viable fertilized eggs from superovulated FVB female mice that had been previously mated to males of the same genetic background. Microinjected viable eggs were transferred into the oviducts of surrogate females. Mice were housed in an environmentally controlled facility maintained on a 7 a.m.–7 p.m. light cycle followed by 7 p.m.–7 a.m. dark cycle. Founder animals were bred to establish transgenic mouse lines in accordance with the procedures of Walsh, et al. (1989) *J. Biol. Chem.* 264:6488–6493, incorporated herein by reference.

EXAMPLE 3

Analysis of Transgenic (MCK-CD36) Mice

At approximately three weeks after birth, each pup was analyzed using DNA taken from the tail. 10 ug of tail tip DNA was digested with PstI, fractionated by agarose gel electrophoresis and blotted on nylon membranes. DNA corresponding to the CD36 minigene was detected with a radiolabeled 1.3 kb BamHI-BamHI CD36 cDNA. RNA isolation and blotting were performed as described previously by Ibrahimi, et al. (1996) *Proc. Natl. Acad. Sci. USA* 93:2646–2651, incorporated herein by reference.

EXAMPLE 4

Seven parameters were studied to assess the role of fatty acid uptake mediated by overexpression of CD36 in the transgenic mice (MCK-CD36) compared to control mice (lacking MCK-CD36): weight gain, plasma free fatty acid levels, triglyceride levels cholesterol levels, plasma lipoprotein levels, body fat and muscle fiber lipid accumulation.

Figure 1:
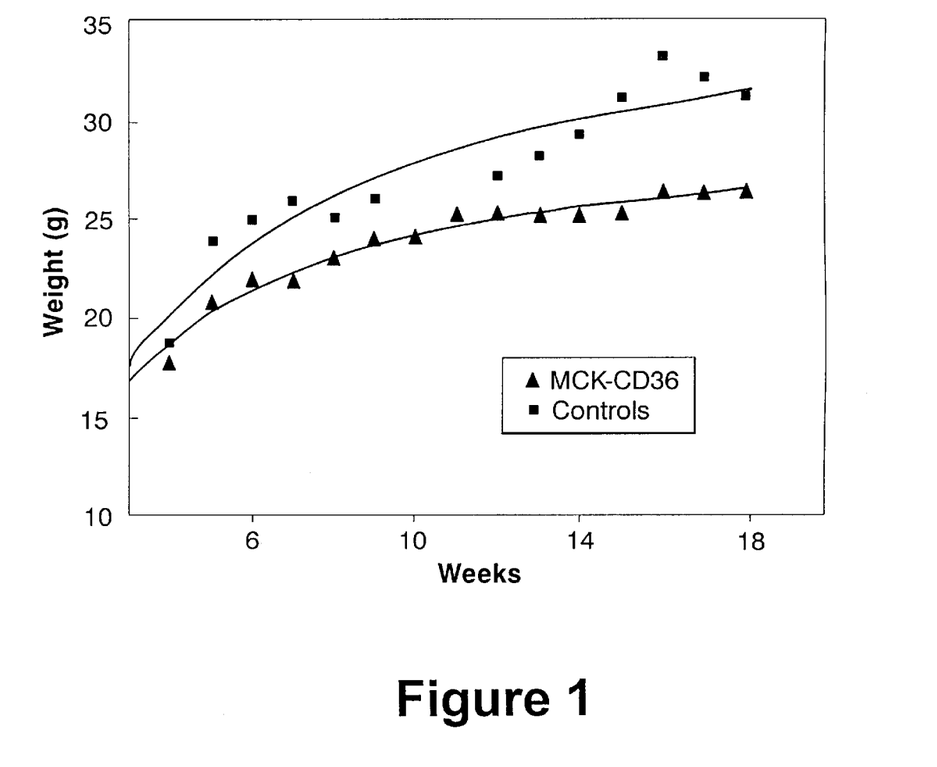
FIG. 1 shows the weight relationship between transgenic mice and control mice over time.

Weight gain for MCK-CD36 transgenic mice and control mice was measured over a period of approximately 18 weeks. The MCK-CD36 mice maintained a lower body weight compared to controls (FIG. 1).

Figure 2:
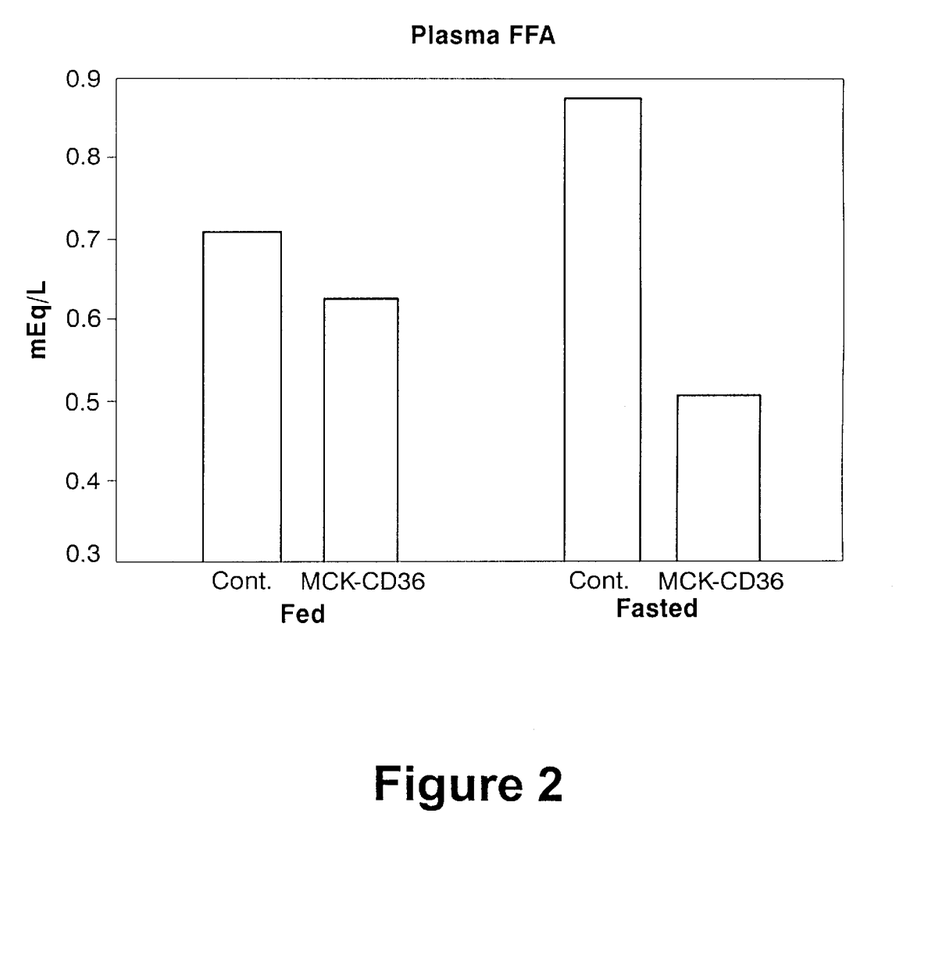
FIG. 2 is a bar graph comparing plasma free fatty acid concentrations of fed and fasted transgenic mice relative to control mice.

Plasma free fatty acid levels were significantly decreased ($p<0.05$) in fed and fasted transgenic mice relative to controls (FIG. 2).

Figure 3:
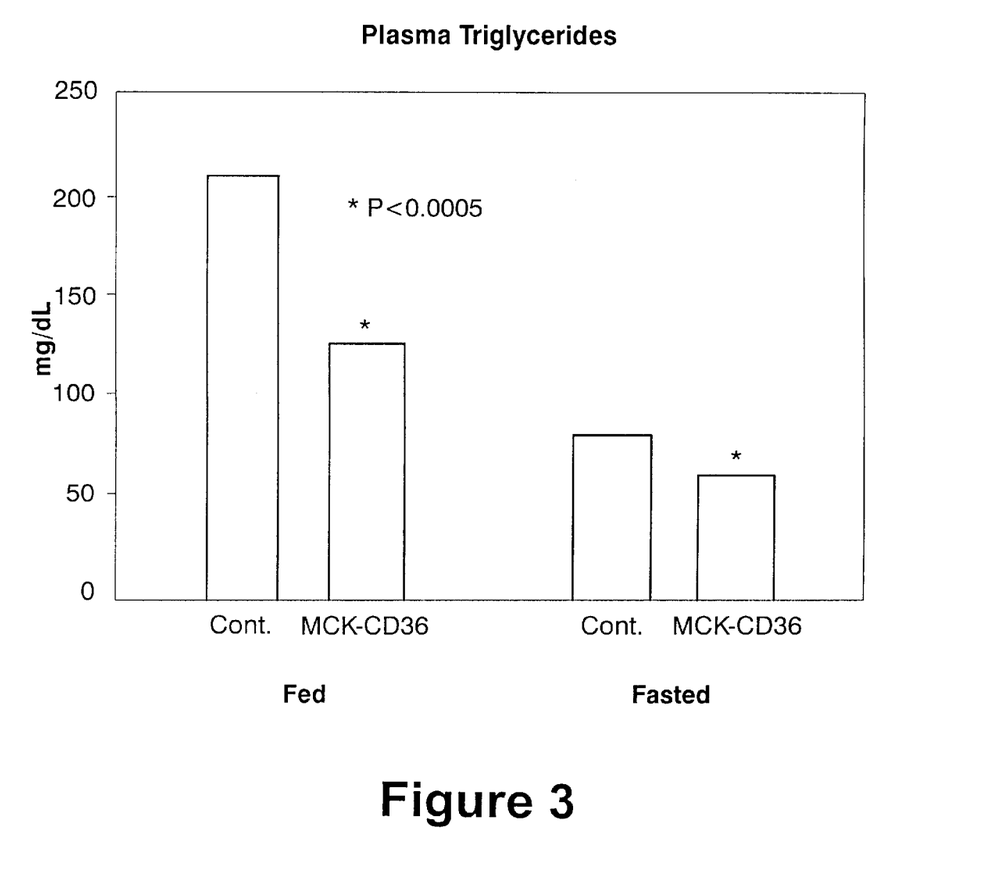
FIG. 3 is a bar graph comparing plasma triglyceride levels in fed and fasted transgenic mice relative to control mice.

Plasma triglyceride levels were significantly decreased ($P<0.0005$) in fed and fasted transgenic mice relative to controls (FIG. 3).

Figure 4:
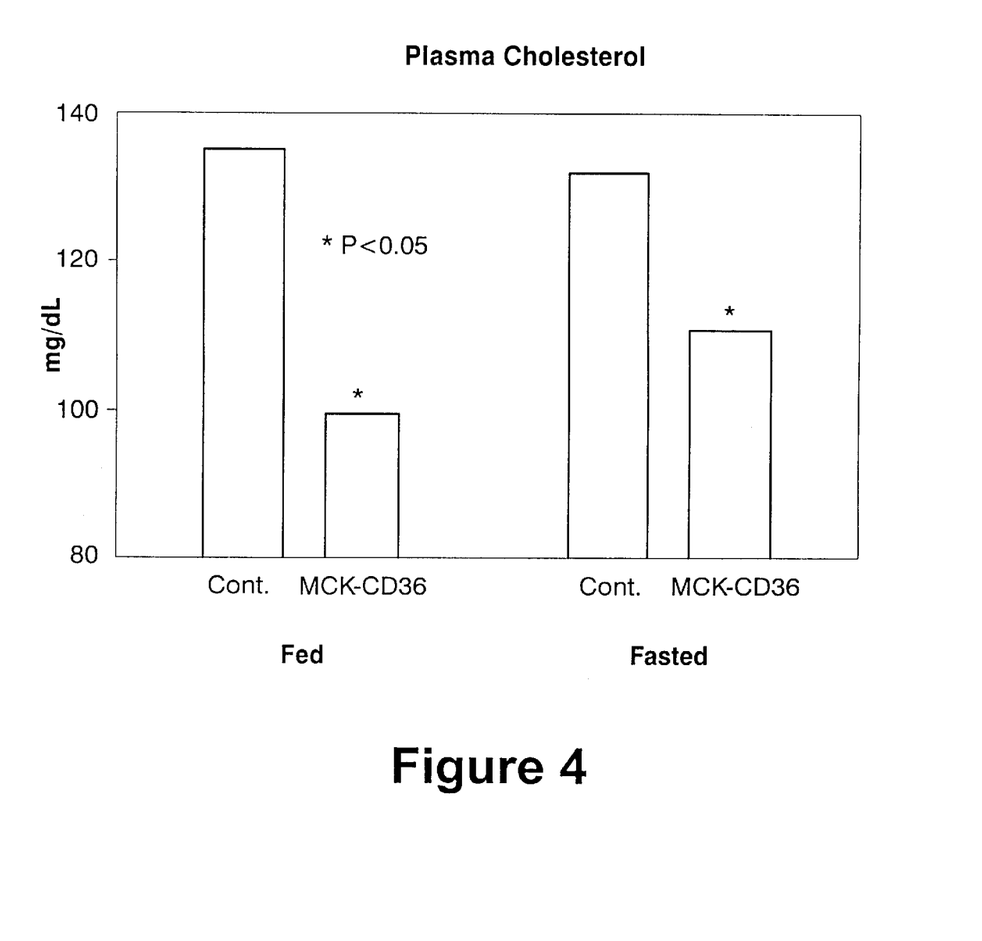
FIG. 4 is a bar graph comparing plasma cholesterol levels in fed and fasted transgenic mice relative to control mice.

Plasma cholesterol levels were significantly decreased ($P<0.05$) in fed and fasted transgenic mice relative to controls (FIG. 4).

Plasma lipoproteins were decreased in fed and fasted transgenic mice relative to controls.

Figure 5A:
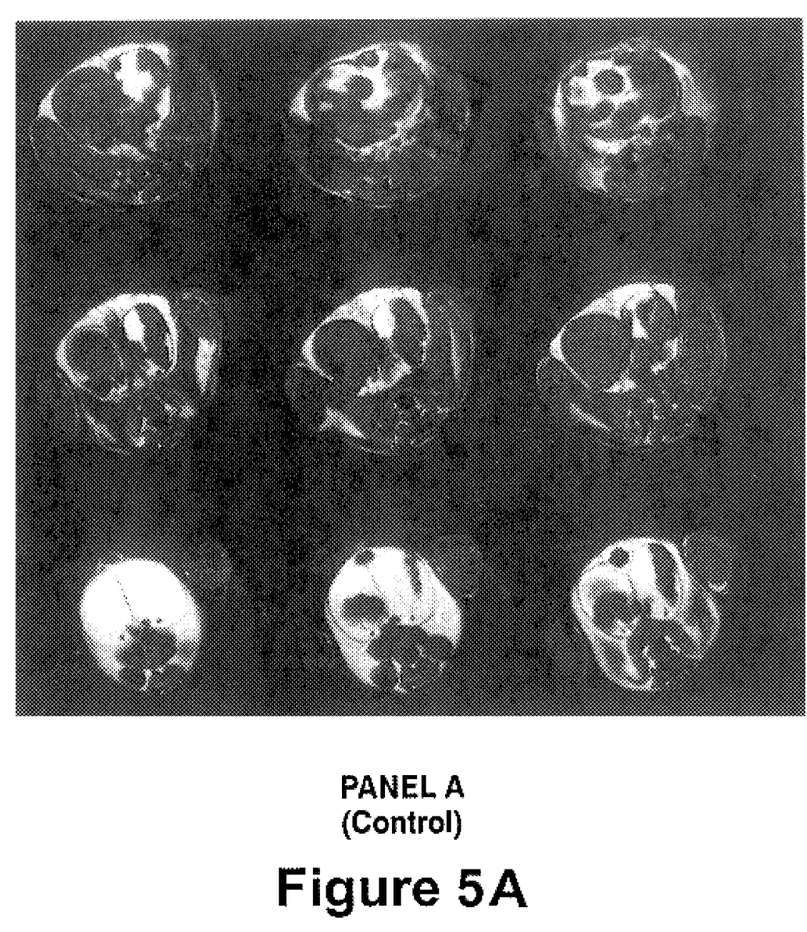
FIGS. 5A and 5B show nuclear magnetic resonance analyses of control (FIG. 5A) and transgenic (MCK-CD36) (FIG. 5B) mice scans show consecutive cross sections of the mouse ending with the tail (left to right). Fat tissue appears bright and contrasts with the remaining tissues.
Figure 5B:
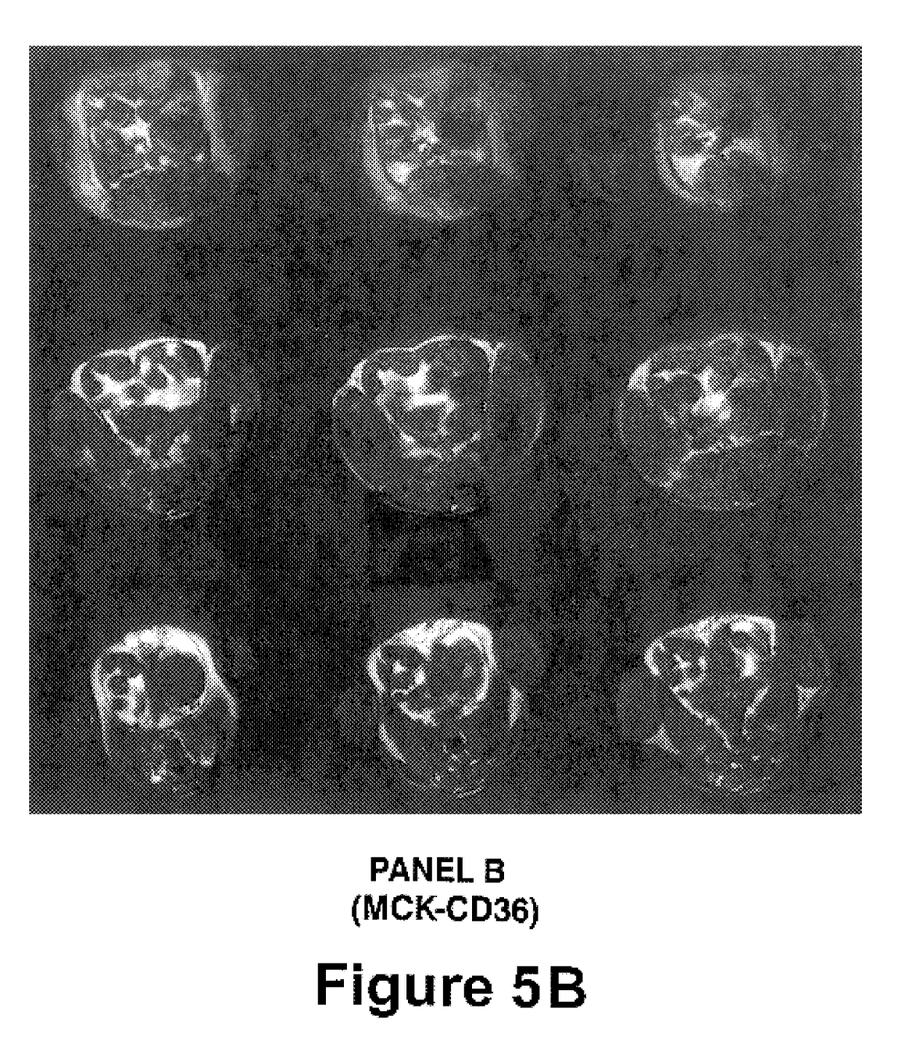
Figure 6A:
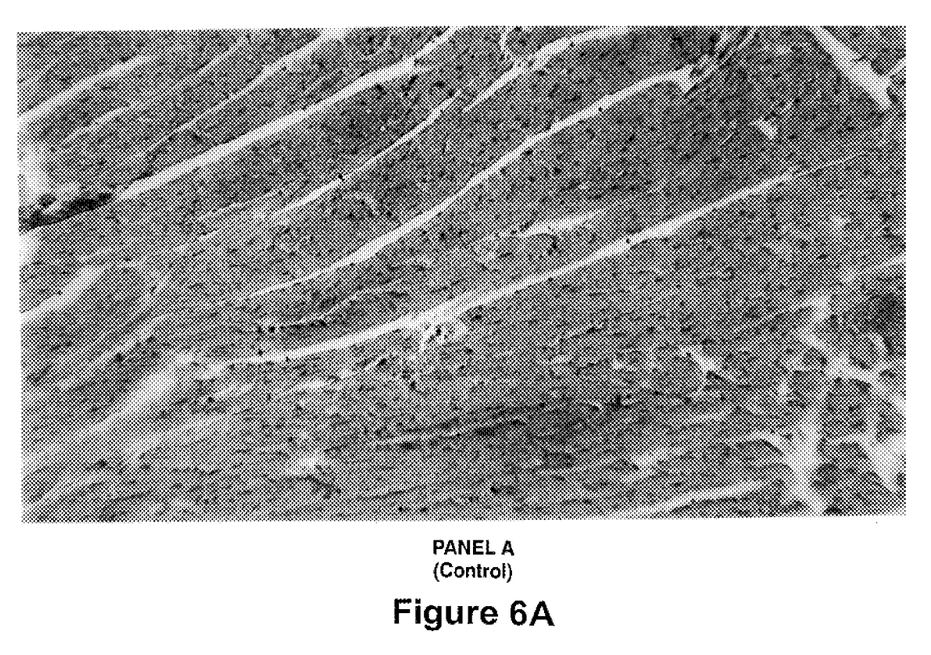
FIGS. 6A and 6B show cryoscopic analyses of heart tissue from control (FIG. 6A) and transgenic (MCK-CD36) mice (FIG. 6B). Heart tissue was stained for lipid with Oil Red O.
Figure 6B:
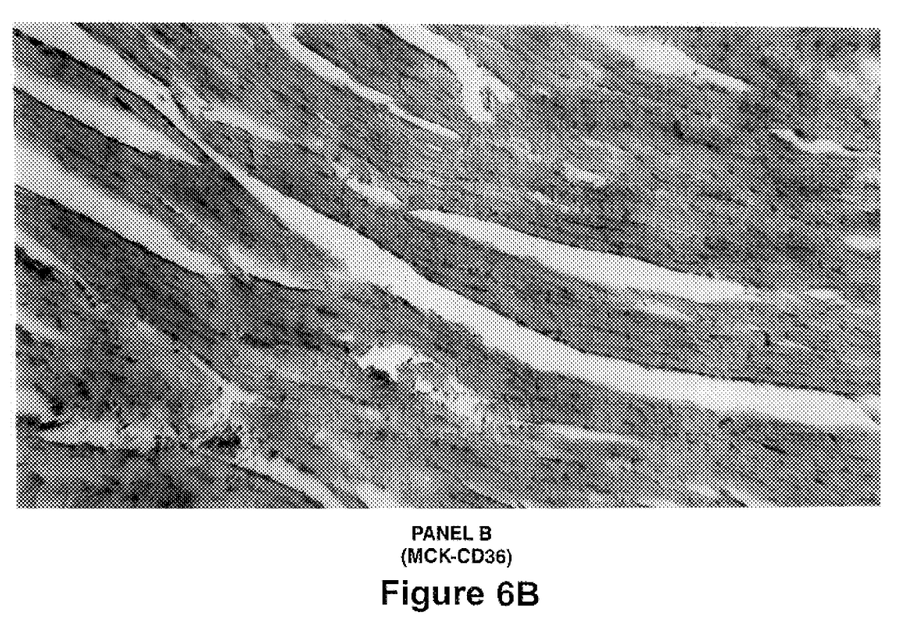

Overall body fat (adipose tissue) was decreased in transgenic (MCK-CD36) animals relative to littermate controls as determined by nuclear magnetic resonance imaging screens (FIG. 5).

Muscle fibers from transgenic (MCK-CD36) mice appeared normal and there were no detectable lipid droplets inside or outside heart muscle fibers. Thus, CD36 expression caused increased FA uptake by muscle, but did not lead to lipid accumulation by the muscle since the FA was oxidized and lysed for energy (FIG. 2).

EXAMPLE 5

Fatty acid oxidation was measured following electrical stimulation of muscles in one hindlimb as compared to control non-stimulated contralateral hindlimb muscles. Hindlimb muscles of one leg were induced to contract by stimulation of the peroneal nerve every 30 minutes while the muscles in the contralateral hindlimb of the same animal were used for the values at rest. Bonen, et al. (1998) *Am. J. Physiol.* 275(3):E471–E478.

Muscles from transgenic (MCK-CD36) mice oxidized more fatty acid, e.g. palmitate, than control littermates. As shown in Table 1, palmitate metabolism (oxidation) was first measured at rest. When the muscles were stimulated to contract, the transgenic animals hindlimb muscles exhibited a significantly greater increased palmitate oxidation compared to non-stimulated contralateral hindlimb controls.

TABLE 1

Palmitate Oxidized by Hindlimb Muscles
From Control and Transgenic MCK-CD36 Mice nmol/g/30 min.

| | Control | | Transgenic | |
|---|---|---|---|---|
| | REST | CONTRACTION | REST | CONTRACTION |
| Oxidation | 15 ± 5.2 | 28.8 ± 2.5 | 22 ± 3.9 | 114.0 ± 42.8* |

*$P < 0.05$, n = 6. Differences in palmitate oxidation with muscle contraction between control and transgenic mice reached statistical significance.

What is claimed is:

1. A transgenic mouse comprising a DNA fragment in the genome, wherein said fragment comprises a CD36 gene which is operably linked to a Muscle Creatine Kinase (MCK) promoter, and said fragment is obtained from plasmid pBS-MCK-CD36 (ATCC deposit # PTA-2727), and wherein said CD36 gene is expressed in the muscle tissue of said mouse at a level sufficient to reduce plasma lipid levels in said mouse relative to a control mouse.

* * * * *